United States Patent [19]
Schafer et al.

[11] Patent Number: 5,873,858
[45] Date of Patent: Feb. 23, 1999

[54] ENDOTRACHEAL TUBE SPLITTER

[75] Inventors: Patrick Schafer; Dwayne Westenskow; Fidel Silva, all of Salt Lake City, Utah

[73] Assignee: University of Utah Research Foundation, Salt Lake City, Utah

[21] Appl. No.: 429,710

[22] Filed: Apr. 27, 1995

[51] Int. Cl.$^6$ .................................................. A61M 5/178
[52] U.S. Cl. .............. 604/161; 128/207.14; 128/207.15; 30/90.4; 30/90.8
[58] Field of Search .................... 604/161, 162, 604/164, 172; 128/207.14, 207.15; 606/172; 30/90.4, 90.8

[56] References Cited

U.S. PATENT DOCUMENTS

| | | | |
|---|---|---|---|
| 3,636,652 | 1/1972 | Dumont | 446/15 |
| 3,831,274 | 8/1974 | Horrocks | 30/90.4 |
| 3,922,779 | 12/1975 | Cormier | 30/90.8 |
| 4,687,469 | 8/1987 | Osypka | 604/161 |
| 4,960,122 | 10/1990 | Mizus . | |
| 4,997,424 | 3/1991 | Little | 604/161 |
| 5,052,386 | 10/1991 | Fischer, Jr. . | |
| 5,188,606 | 2/1993 | Maloney et al. . | |
| 5,261,887 | 11/1993 | Walker . | |
| 5,330,460 | 7/1994 | Moss et al. | 604/161 |

FOREIGN PATENT DOCUMENTS 704488  2/1954  United Kingdom .................... 30/90.4

*Primary Examiner*—Robert A. Hafer
*Assistant Examiner*—Justine R. Yu
*Attorney, Agent, or Firm*—Thorpe, North & Western, L.L.P.

[57] ABSTRACT

An endotracheal tube splitter and a method for removing an endotracheal tube are disclosed. The endotracheal tube splitter includes a handle portion, a cutting edge for cutting the endotracheal tube as it is withdrawn from a patient, and a support member for preventing the cutting edge from turning to either side and for maintaining the cutting edge at least a minimum desired distance from the face of the patient. The endotracheal tube splitter allows the more rapid replacement of the endotracheal tube, and allows a bronchoscope to be used as the guide for placing the tube.

9 Claims, 6 Drawing Sheets

ENDOTRACHEAL TUBE SPLITTER

BACKGROUND OF THE INVENTION

The present invention relates to a device and method for removing and replacing an endotracheal tube, and in particular to an endotracheal tube splitter for facilitating the replacement of endotracheal tubes.

The use of endotracheal tubes to facilitate mechanical respiration or ventilation in certain hospital and nursing home patients with various respiratory problems is well known to those skilled in the art. The tube is usually passed through the patient's mouth or nose so that a bottom end of the tube fits snugly in the patient's trachea, while a top end remains extending out of the patient's mouth or nose. In this position, the endotracheal tube enables the patient to be mechanically ventilated or to breath freely, uninterrupted by the respiratory disorder or other limitations.

For a variety of reasons, such as the prevention of infections or the failure of a cuff disposed along the tube, the endotracheal tube must be replaced periodically. Prior to the present invention, this was done by sliding one end of an elongate guide down the endotracheal tube and gently sliding the endotracheal tube out of the patient and over an opposing end of the guide. The replacement endotracheal tube was then slid onto the guide, and then down the guide until it lodged in the proper place in the trachea. A guide for replacing the endotracheal tube in this manner is shown in U.S. Pat. No. 4,960,122.

As will be appreciated by those skilled in the art, this approach has several limitations. First, time is of the essence when replacing the endotracheal tube, as removal and replacement of the tube causes disturbances to the patient's ability to breath. Taking the old endotracheal tube off the guide and threading on the new endotracheal tube adds time to the procedure. Second, such an approach inhibits the use of a bronchoscope during the procedure, instead relying on a simple guide. If a bronchoscope were to be used in accordance with the teachings of the prior art, the limitations of the endotracheal tube would require that the end of the bronchoscope outside of the patient must have an ending which is no bigger than the inner diameter of the endotracheal tube, or an end which is detachable.

In accordance with the present invention, it has been found that splitting the endotracheal tube as it is withdrawn from the patient's mouth provides a superior method for replacing the tube. First, the time to replace the endotracheal tube is reduced by splitting the tube as it is withdrawn so that the replacement tube can be prethreaded over the bronchoscope. Second, the splitting of the tube allows a bronchoscope to be used to view the trachea of the patient as the tube is being withdrawn and as the replacement tube is positioned in the trachea.

The use of a cutting device to remove a tube is not new. For several years the thin tubes used for introducing catheters have been cut as they are withdrawn from the patient. However, there are several important differences between using a cutting device to remove a catheter introducer and an endotracheal tube. First, when cutting an introducer, time is generally not of the essence. The introducer may be withdrawn at any comfortable rate. Second, in most catheter arrangements, the opposing end of the catheter is well placed in the body and slight jerks on the catheter line will not displace the catheter. Third, the introducer tubing is generally soft and flexible.

In contrast, when removing a endotracheal tube, time is of the essence. Typically, the tube must be removed and replaced within about 30 seconds. Additionally, the endotracheal tube must be removed very carefully in that a sudden jerk will often displace the end of the bronchoscope from the trachea into the patient's esophagus. Furthermore, the endotracheal tube is relatively rigid and typically much more difficult to cut than is the tubing of the introducer.

An additional concern with the catheter introducer cutting devices of the prior art is that many have a relatively exposed blade. Because of the introduction location of most catheters, significant protection around the blade is not needed. Even if a slip does occur, the cutter will only cause a small cut to the skin of the patient. In contrast, the use of such a cutter to split an endotracheal tube would be extremely dangerous adjacent the face, as a slip could result in cutting the patient's lip, nose, or worse, putting out the patient's eye.

Thus, there is a substantial need for a endotracheal tube splitter which safely and efficiently splits an endotracheal tube as it is removed from a patient so that a replacement tube may be quickly positioned in the trachea.

SUMMARY OF THE INVENTION

It is an object of the invention to provide an endotracheal tube splitter for use in replacing endotracheal tubes.

It is another object of the invention to provide such a tube splitter which is inexpensive and easy to use.

It is another object of the invention to provide a method for removing and replacing an endotracheal tube.

It is a further object of the invention to provide an endotracheal tube splitter which protects the face of the patient from accidental lacerations as the tube is withdrawn and replaced with a new endotracheal tube.

The above and other objects of the invention are realized in specific illustrated embodiments of an endotracheal tube splitter including a handle for holding the tube splitter, and a cutting portion attached to the handle. The cutting portion includes a cutting blade, a guide and a plurality of curvatures to cut the endotracheal tube, and to prevent the cut tube from accidentally catching on the bronchoscope and dislodging the bronchoscope from the trachea of the patient as the tube is removed.

In accordance with another aspect of the invention, a support is provided to prevent the cutting portion of the endotracheal tube splitter from accidentally contacting the face of the patient. The support may be a member extending from the handle which contacts the face of the patient, or may be a restraining device which attaches to some other object in order to prevent the endotracheal tube splitter from passing below a certain point and into contact with the patient's face.

In accordance with yet another aspect of the invention, the endotracheal tube splitter includes an alignment mechanism to ensure that the endotracheal tube is withdrawn and cut at the proper angle.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
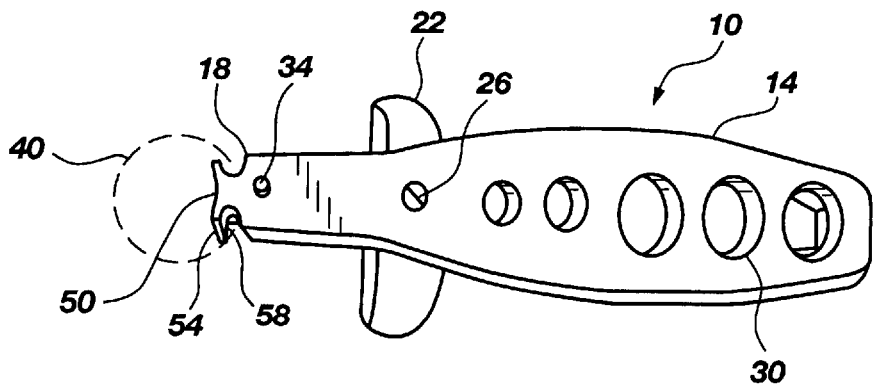
FIG. 1 shows a top view of an endotracheal tube splitter made in accordance with the principles of the present invention.

Reference will now be made to the drawings in which the various elements of the present invention will be given numeral designations and in which the invention will be discussed so as to enable one skilled in the art to make and use the invention. Referring to FIG. 1, there is shown an endotracheal tube splitter, generally designated at 10. The tube splitter 10 includes a handle portion 14, a cutting portion 18, and a support member 22 which extends from the handle portion in a manner discussed in FIG. 2. The support member 22 is typically attached to the handle portion 14 by a screw 26 or some other convenient fastening device.

As shown in FIG. 1, the handle portion 14 has a plurality of holes, such as hole 30, which are present to enable the handle portion to be of a comfortable size to be gripped by a human hand without excess weight or waste of materials. Typically, the handle portion 14, the support member 22 and most portions of the cutting portion 18 will be made of a lightweight, durable polycarbonate material. However, other materials such as surgical steel could also be used.

On the handle portion 14, adjacent the cutting portion 18 may be disposed a sight alignment 34 for ensuring that the endotracheal tube splitter 10 is properly aligned as it moves along the endotracheal tube, represented by the dashed lines 40.

As will be explained in additional detail with respect to FIG. 2, the cutting portion 18 has several curvatures which help the endotracheal tube splitter 10 to cut the endotracheal tube 40 quickly and with little disturbance to the bronchoscope (not shown) which is used to place the replacement endotracheal tube. The curvature 50, in the forwardmost end 54 of the cutting portion 18 is generally concave so as to protect the bronchoscope which is typically made of a fiber optic cable covered in a vinyl sheath. Its radius of curvature is typically slightly larger than an outer radius of curvature for a bronchoscope. A pair of curvatures 58 slightly behind the forwardmost end 54 of the cutting portion 18 form a wedge so as to force apart opposing sides of the split endotracheal tube 40 so that the sides do not grab the bronchoscope as the endotracheal tube is pulled out of the patient's mouth and off of the bronchoscope.

Figure 2:
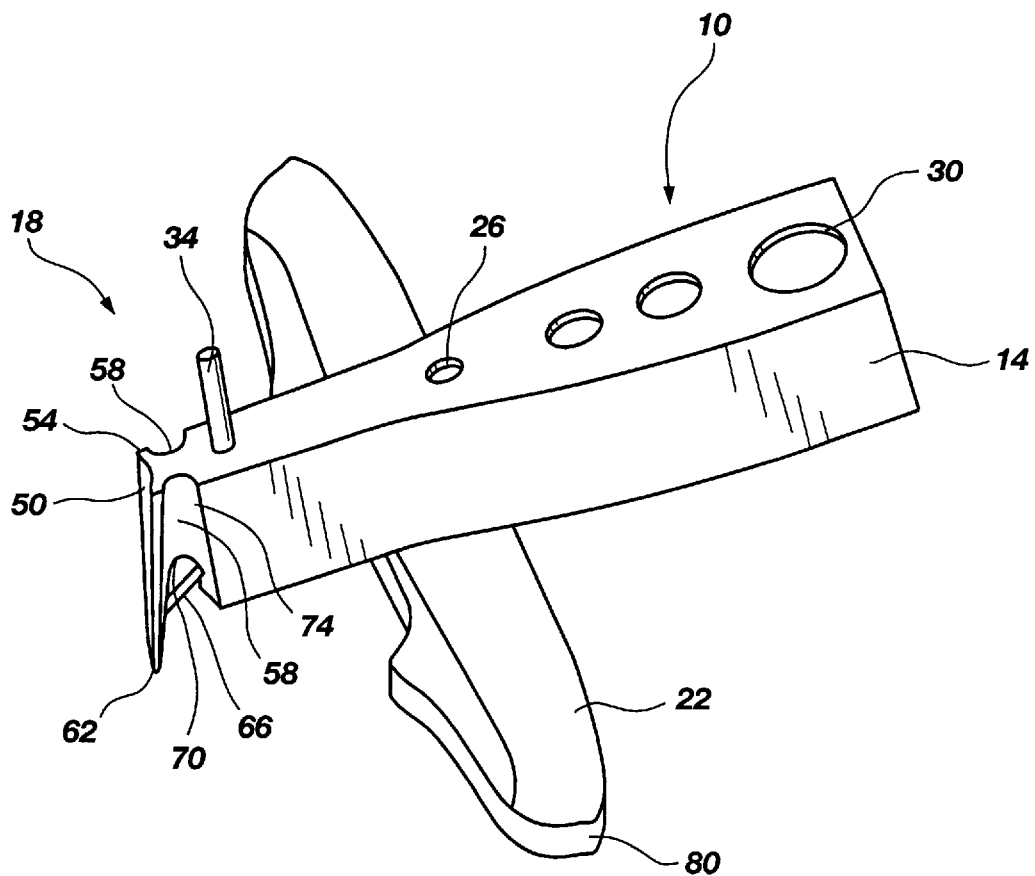
FIG. 2 shows a fragmented side view of the endotracheal splitter of FIG. 1, including the cutting portion of the splitter.

Referring now to FIG. 2, there is shown a fragmented perspective view of the endotracheal tube splitter 10 discussed regarding FIG. 1 and numbered accordingly. The forwardmost end 54 of the cutting portion 18 extends downward to a elongate point so as to form a lip guide 62. The lip guide 62 helps to prevent the cutting portion from rotating to either side while cutting through the tube.

Figure 4A:
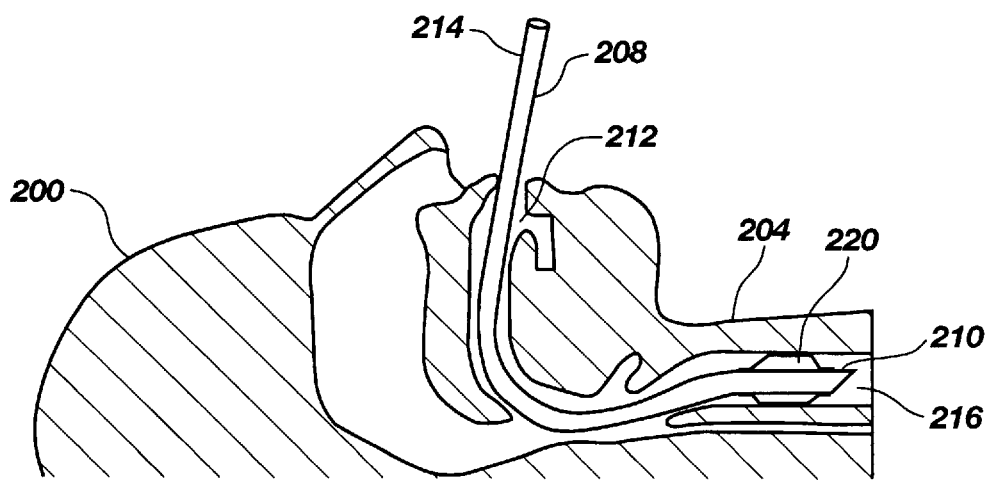
FIGS. 4A through 4E show a cross-sectional view of a human head and neck with an endotracheal tube positioned therein, and demonstrate the steps of replacing an endotracheal tube in accordance with the teachings of the present invention.
Figure 4B:
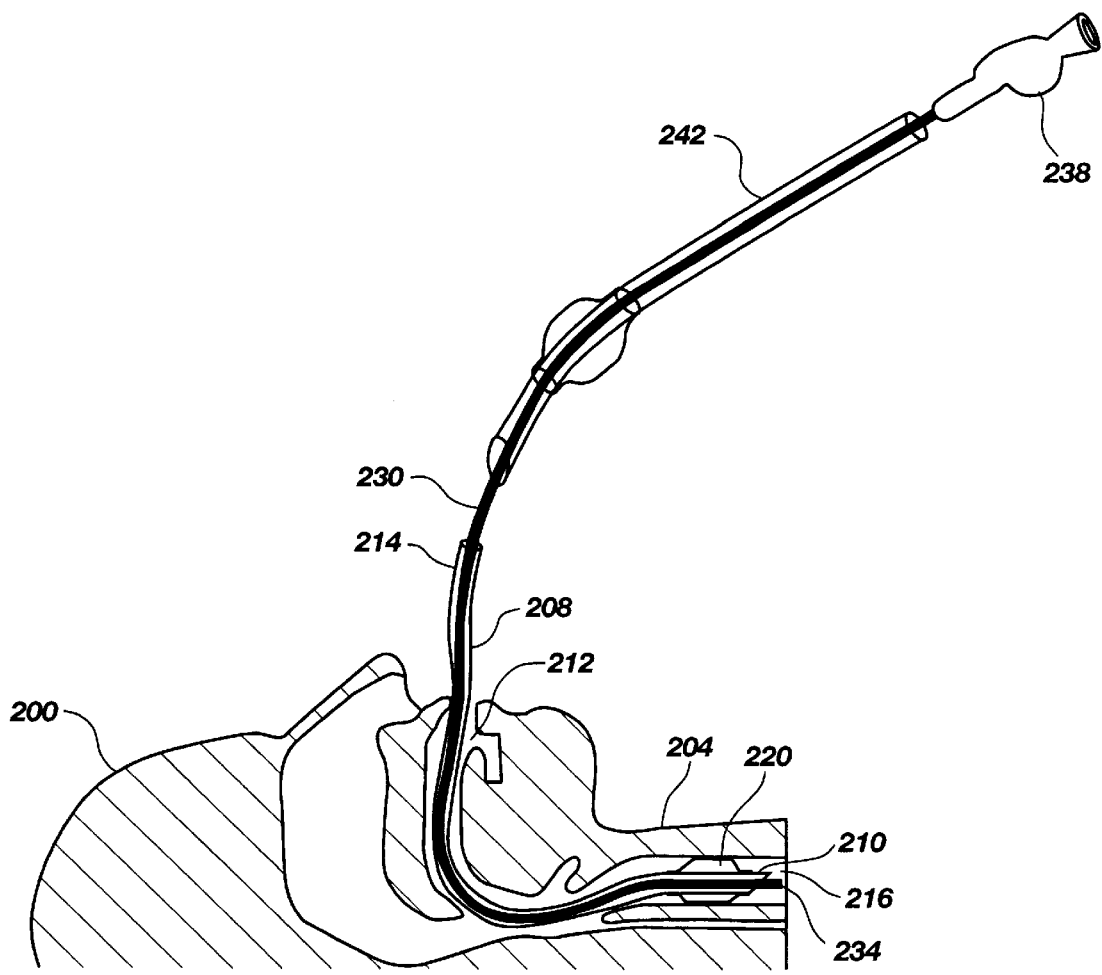
Figure 4C:
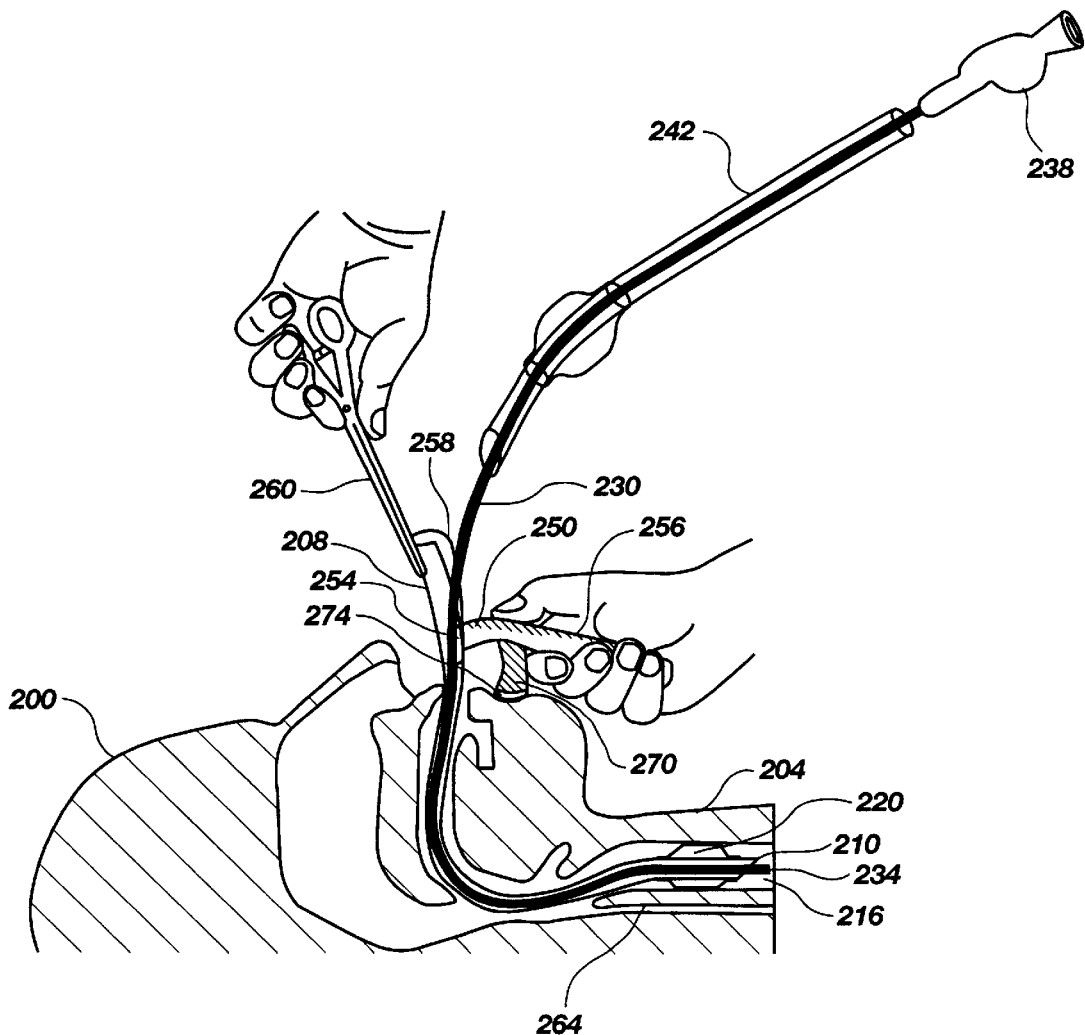
Figure 4D:
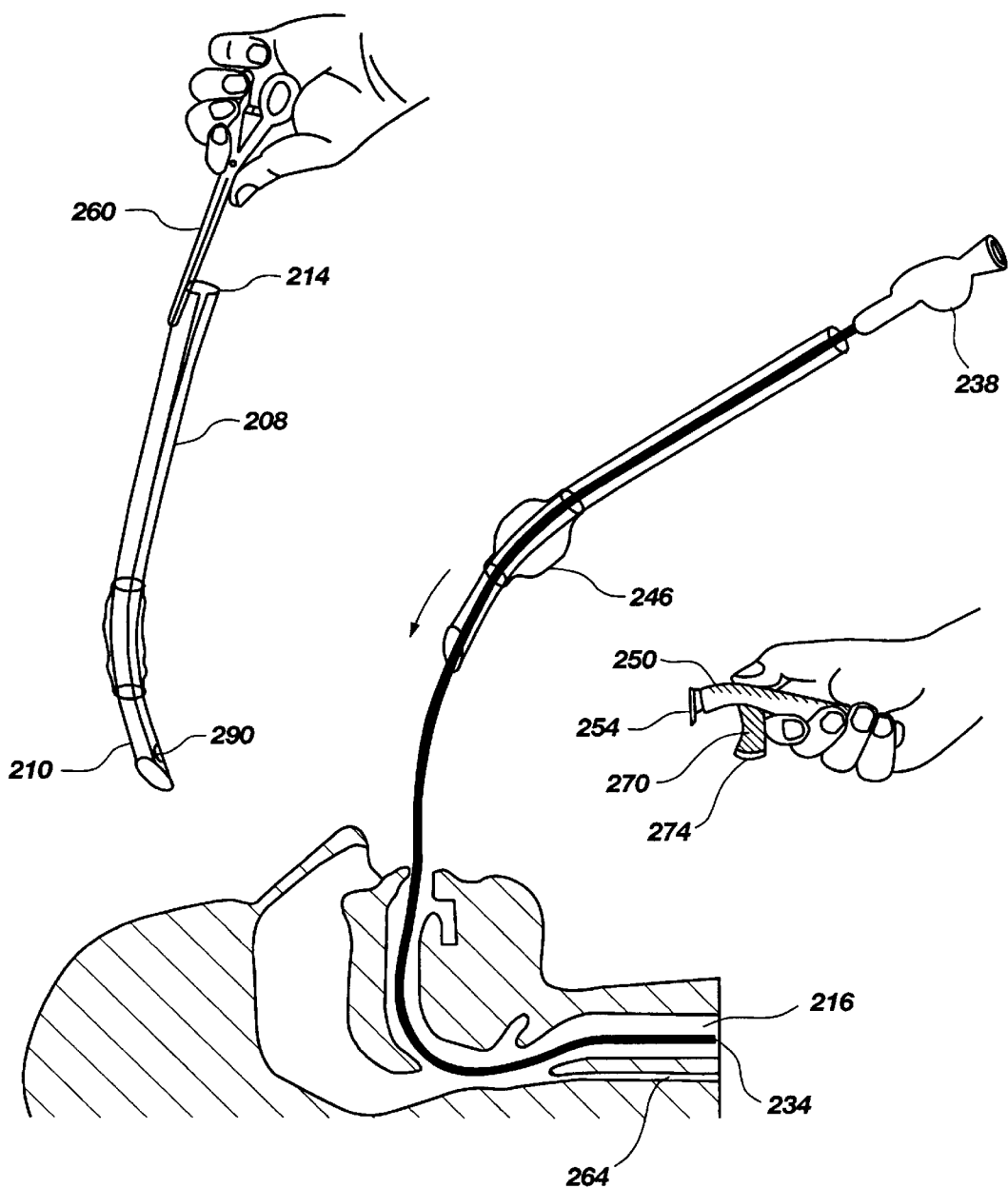

Those skilled in the art will recognize that a significant problem in removing endotracheal tubes is a small hole formed in the tube near its end, commonly referred to as a Murphy's eye (290 FIG. 4D). If the cutting device is not designed properly, the cutting blade may come out of the endotracheal tube as it passes through Murphy's eye. This can cause two major problems. First, the sudden change in resistance may cause the medical personnel withdrawing the tube to slip and lacerate the face of the patient. Second, the removal of the cutting blade leaves a small length of tube uncut and prevents rapid replacement with another endotracheal tube. By providing the elongate lip guide 62, the problem presented by Murphy's eye is overcome, as the guide keeps the cutting blade 66 in the proper position so as to finish the cutting.

Above the cutting blade 66, the curvatures 58 taper to a point 70 so as to form a wedge. As the cutting blade 66 passes through a wall of an endotracheal tube, the wedge formed by the curvatures 58 forces the two sides of the cut endotracheal tube apart so that they will not catch on the bronchoscope as the endotracheal tube is removed (See FIG. 4C). The rearward most portion 74 of the curvatures 58 is broadly rounded so that it will not catch on the inflatable cuff (FIG. 4A) near the bottom of the endotracheal tube as it is drawn past the cutting blade 66.

Also shown in FIG. 2, the support member 22 will typically have a broad base layer 80 made of a force absorbing, slip resistant material. As the endotracheal tube splitter 10 is used to cut the endotracheal tube being removed, a significant amount of force can be placed on the face of the patient. The material prevents bruising to the face of the patient, and prevents the support member 22 from slipping on the patient's face during removal of an endotracheal tube. The material used for the base layer 80 will typically be foam rubber or an elastomeric material. Preferably, the support member 22 and base layer 80 will hold the cutting blade 66 between one and three inches from the face of the patient. However, any distance of at least one inch will generally be sufficient.

The broad base layer 80 also rests snugly against the patient's face to minimize the tendency of the cutting portion 18 to turn to either side. By keeping the cutting blade 66 balanced and oriented straight down, the tube is cut more efficiently and correctly on the first attempt.

Figure 3:
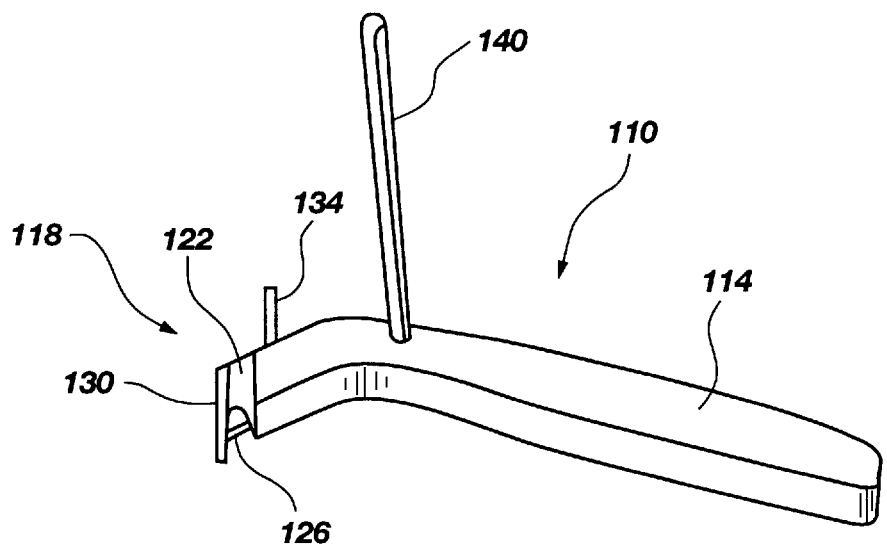
FIG. 3 shows an alternate embodiment of the invention to that shown in FIGS. 1 and 2.

Referring now to FIG. 3, there is shown another embodiment of the present invention. The endotracheal tube splitter 110 includes a handle portion 114, and a cutting portion 118, including curvatures 122, and a cutting blade 126 adjacent the forwardmost end 130. A sight alignment 134 is also provided in a position generally parallel to a cutting plane of the cutting blade 126 so that the user may be assured that the cutting blade is not rotating to either lateral side.

In contrast to the embodiment discussed in FIGS. 1 and 2, however, a support member does not extend downward from the handle portion 114 so as to rest on the face of a patient. Instead, a support band 140 is provided which extends from the upper surface of the handle portion. The support band 140 may be made of several different lengths so that it may be attached to a convenient base, such as an IV bottle stand or some sort of stable overhead device. The length of the support band 140 is selected so that at full extension, the band holds the handle portion 140 one to three inches above the patient's face. In the event the person using the splitter 110 slips while cutting the endotracheal tube, the support band 140 will prevent the cutting blade 126 from contacting the patient. The support band 140 also helps the user to prevent rotation of the blade 126, as would be evidenced by the slight alignment 134.

In FIGS. 4A through 4E, there is shown the steps which would normally be conducted in removing an endotracheal tube from a patient and replacing it with a new endotracheal tube. Referring specifically to FIG. 4A, there is shown a cross-sectional view of human head 200 and neck 204. An endotracheal tube 208 is placed so that a first end 210 is positioned in the patient's trachea 216 and a second end 214 extends out of the patient's mouth 212. An inflatable cuff 220 is provided to seal between the endotracheal tube 208 and the trachea, thereby allowing protection of the airway against aspiration and allowing mechanical ventilation.

Referring now to FIG. 4B, a bronchoscope 230 is slid into the endotracheal tube 208 so that a proximal end 234 of the bronchoscope extends slightly past the endotracheal tube in the trachea 216. Prior to the present invention, an elongate guide (not shown) would be positioned into the endotracheal tube 208 as is the bronchoscope 230. The endotracheal tube 208 would be slid out of the patient's mouth and off of the guide. A replacement endotracheal tube would then be slid onto the guide and slid into the position previously occupied by the removed endotracheal tube 208. In the present invention, however, there is no need to use a simple guide, and no need to remove the old endotracheal tube before loading the replacement endotracheal tube. As is shown in FIG. 4B, the replacement endotracheal tube 242 is preloaded on a bronchoscope 230 which can be used to view the trachea 216 during the procedure.

Referring now to FIG. 4C, the endotracheal tube splitter 250 is positioned so that the lip guide 254 extends down into the endotracheal tube 208. A pair of forceps 260 or a similar holding device is used to grab the endotracheal tube and slowly remove it from the patient thereby drawing the endotracheal tube away from the patient's face. The forceps 260 are helpful because the tubing of the endotracheal tube 208 is slippery and difficult to cut and hold by hand.

As the old endotracheal tube 208 is pulled from the patient's mouth 212, the endotracheal tube splitter 250 cuts the endotracheal tube 208 and pushes apart the cut sides 258 of the tube so that they do not catch on the bronchoscope 230. This is important because jarring the bronchoscope 230 could dislodge it from the trachea 216 and cause it to become lodged in the esophagus 264.

For additional stability, and to prevent the lip guide 254 or the cutting blade (not shown) from contacting the patient, the support member 270 is positioned so that the base layer 274 extends transverse with respect to the handle 256 and rests on the chin or other portion of the patient's face. The base layer 274 prevents the force accompanying the cutting of the old endotracheal tube 208 from bruising the patient, and also prevents the support member 270 from slipping on the patient's skin.

Figure 4E:
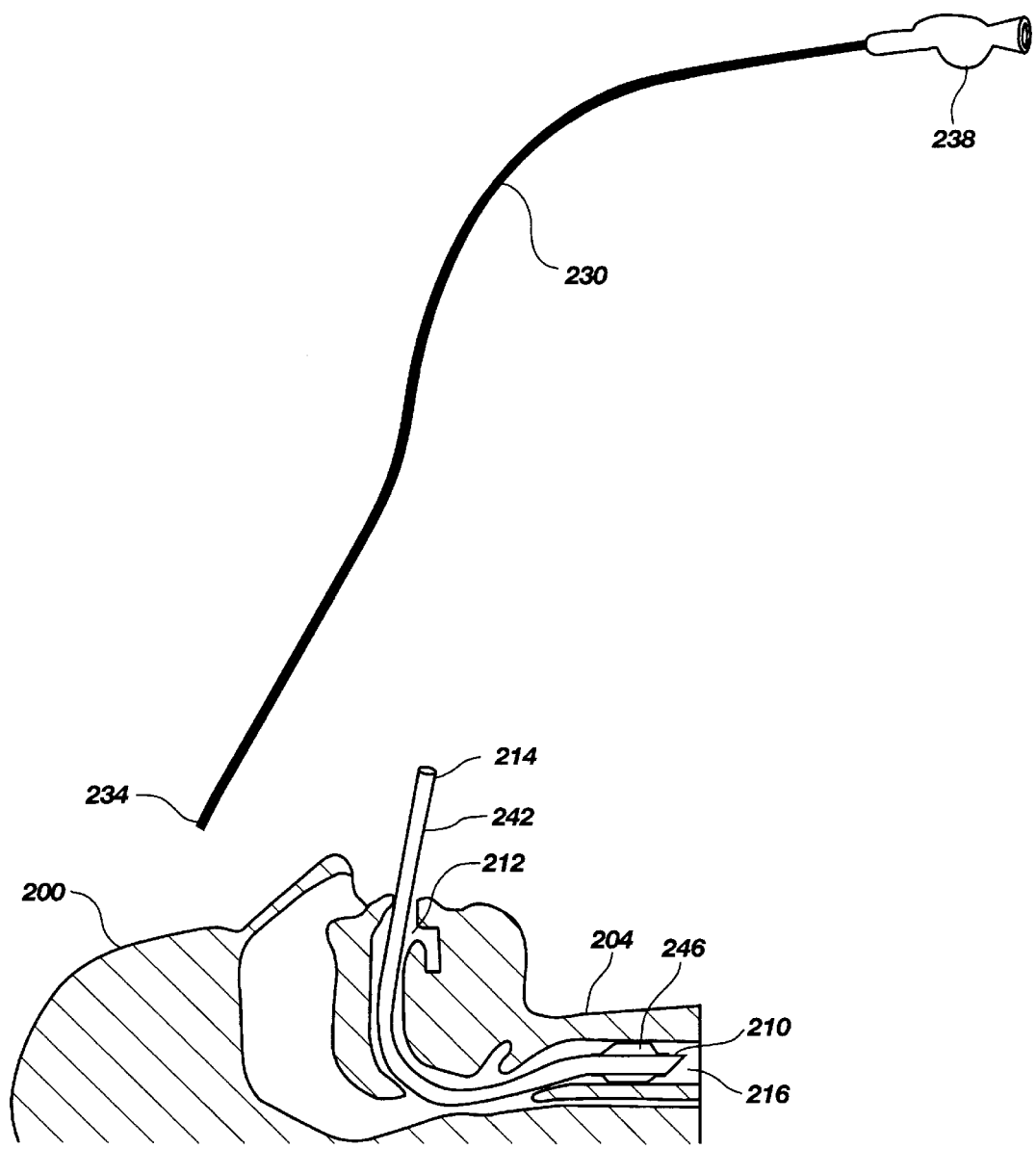

Because the old endotracheal tube 208 has been cut through its entire length (including Murphy's eye 290), it may be removed from the bronchoscope 230 quickly and easily, as is shown in FIG. 4D. Once the old endotracheal tube 208 has been removed, the endotracheal tube splitter 250 is put away and the new endotracheal tube 242 is slid along the bronchoscope 230 until the cuff 246 of the endotracheal tube 242 is lodged properly in the trachea 216. The bronchoscope 230 is then withdrawn, as shown in FIG. 4E, leaving the new endotracheal tube 242 in its proper place.

The endotracheal tube splitter 250 allows the removal and replacement of the old endotracheal tube 208 safely and efficiently in about 30 to 40 seconds or less. This small amount of time is easier on the patient, and is less complicated for medical personnel.

Thus there is disclosed an endotracheal tube splitter for removing endotracheal tubes and a method for replacing endotracheal tubes. Those skilled in the art will recognize numerous modifications which can be made to the splitter without departing from the scope and spirit of the invention. The appended claims are intended to cover such modifications.

What is claimed is:

1. An endotracheal tube splitter for removing endotracheal tubes from an inhibating position within a patient wherein a first end of the endotracheal tube is disposed in the trachea and a second end is adpated to be disposed outside the patient, the splitter comprising:

handle means configured for gripping by a human hand;

cutting means connected to the handle means for cutting through the endotracheal tube from the second end to the first end as the tube is withdrawn from the patient, stabilizing support means coupled to the handle means for inhibiting rotation of the cutting means so as to facilitate cutting of the endotracheal tube in a generally straight line continuously between the second and first ends, and for holding the cutting means at least a predetermined minimum distance from the patient, wherein the cutting means comprises a cutting blade and a forwardmost end defining a guide means for insertion into the endotracheal tube and for guiding the cutting blade along the endotracheal tube, and wherein the guide means comprises a first side for sliding along the endotracheal tube and a second, forwardmost side having a concave curvature.

2. The endotracheal tube splitter of claim 1, wherein the endotracheal tube splitter is configured for cutting an endotracheal tube from about a bronchoscope having a convex outer surface disposed within the endotracheal tube, and wherein the second, forwardmost side has a radius of curvature of at least as large as the outer surface of the bronchoscope.

3. An endotracheal tube splitter for removing endotracheal tubes from an inhibating position within a patient wherein a first end of the endotracheal tube is disposed in the trachea and a second end is adpated to be disposed outside the patient, the splitter comprising:

handle means configured for gripping by a human hand;

cutting means connected to the handle means for cutting through the endotracheal tube from the second end to the first end as the tube is withdrawn from the patient, stabilizing support means coupled to the handle means for inhibiting rotation of the cutting means so as to facilitate cutting of the endotracheal tube in a generally straight line continuously between the second and first ends, and for holding the cutting means at least a predetermined minimum distance from the patient, wherein the stabilizing support means comprises a support member extending generally downwardly from the handle means for resting on the patient's face; and wherein the support member has an upper portion for attachment to the handle means and a broad base portion extending transverse with respect to the handle means for resting on the patient's face.

4. The endotracheal tube splitter of claim 3, wherein the cutting means further comprises a pair of lateral sidewalls forming a wedge above the cutting blade for deflecting cut sides of the endotracheal tube away from one another.

5. The endotracheal tube splitter of claim 4, wherein the wedge comprises generally concave curved sidewalls.

6. The endotracheal tube splitter of claim 3, wherein the stabilizing support means extends downwardly so as to hold the cutting means at least one inch from the patient's face.

7. The endotracheal tube splitter of claim 3, wherein the base portion comprises a base layer disposed at an end of the base portion opposite the upper portion, the base layer comprising a slip resistant surface.

8. The endotracheal tube splitter of claim 3, wherein the base portion comprises a base layer disposed at an end of the base portion opposite the upper portion, the base layer comprising a force absorbing material.

9. The endotracheal tube splitter of claim 3, further comprising sight alignment means positioned generally parallel with a cutting plane of the blade for assisting in proper alignment of the cutting means and minimizing rotation of the blade to either lateral side.

* * * * *